United States Patent [19]

Gramlich et al.

[11] Patent Number: 4,757,051
[45] Date of Patent: Jul. 12, 1988

[54] 2-TERT-BUTYL-4-METHYLCYCLOHEXANOL DERIVATIVES, THEIR PREPARATION AND THEIR USE AS SCENTS

[75] Inventors: Walter Gramlich, Edingen-Neckarhausen, Fed. Rep. of Germany; Werner Hoffman, New York, N.Y.; Ludwig Schuster, Limburgerhof, Fed. Rep. of Germany

[73] Assignee: BASF Aktiengesellschaft, Rheinland-Pfalz, Fed. Rep. of Germany

[21] Appl. No.: 84,163

[22] Filed: Aug. 11, 1987

[51] Int. Cl.⁴ ................................................ A61K 7/46
[52] U.S. Cl. ........................................ 512/23; 512/22; 568/579; 568/658; 568/834
[58] Field of Search ................... 512/23, 22; 568/658, 568/579, 832, 834

[56] References Cited
U.S. PATENT DOCUMENTS
2,450,877 10/1948 Carptenter et al. ................ 568/658

Primary Examiner—Werren B. Lone

Attorney, Agent, or Firm—Oblon, Fisher, Spivak, McClelland & Maier

[57] ABSTRACT

Novel 2-tert-butyl-4-methylcyclohexanol derivatives of the general formula I

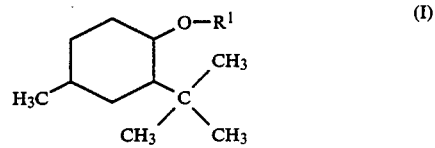

where $R^1$ is alkyl of 1 to 3 carbon atoms or an acyl group

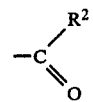

where $R^2$ is alkyl of 1 to 5 carbon atoms, and a process for their preparation, their use as scents, and scent compositions containing compounds of the formula I.

Particularly interesting compounds are 2-tert-butyl-4-methylcyclohexyl acetate and propionate.

6 Claims, No Drawings

2-TERT-BUTYL-4-METHYLCYCLOHEXANOL DERIVATIVES, THEIR PREPARATION AND THEIR USE AS SCENTS

The present invention relates to 2-tert-butyl-4-methylcyclohexanol derivatives of the general formula I

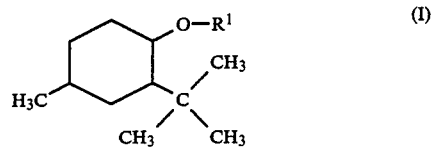

where $R^1$ is alkyl of 1 to 3 carbon atoms or an acyl group

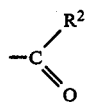

where $R^2$ is alkyl of 1 to 5 carbon atoms. Acyl groups, in particular acetyl, are preferred.

Because of the general lack of sufficient quantities of many natural scent components, the necessity of adapting to changing tastes in fashion, and the steadily growing demand for odor improvers for products of daily use, such as cleaning agents, cosmetics, glues, etc., the fragrance industry is in constant need of novel scents which, alone or in the form of compositions, constitute useful perfumes or fragrance materials with interesting fragrance notes. Little is known about the relationships between structure and fragrance properties, making it impossible to synthesize scents having the desired olfactory properties in a controlled manner. There is therefore a need to find compounds which have useful fragrance qualities.

It is an object of the present invention to provide novel interesting scents which can be prepared in a very simple manner from readily available and hence cheap and commercially available starting materials.

We have found that this object is achieved by 2-tert-butyl-4-methylcyclohexanol derivatives of the formula I, which can be prepared in a simple manner from readily available starting materials and some of which have extremely interesting fragrance properties.

The starting material for the preparation of the novel compounds is 2-tert-butyl-4-methylphenol, which can readily be prepared from p-cresol by tert-butylation with isobutylene and is also commercially available. This dialkylphenol is either first acylated or alkylated and then subjected to hydrogenation in the nucleus, or is first hydrogenated to the 2-tert-butyl-4-methylcyclohexanol and then acylated or alkylated.

The present invention therefore also relates to a process for the preparation of 2-tert-butyl-4-methylcyclohexanol derivatives of the general formula I, wherein a 2-tert-butyl-4-methylphenol derivative of the general formula II

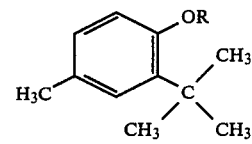

where R is hydrogen or has the above meanings, is either hydrogenated and then esterified or etherified, or esterified or etherified and then hydrogenated.

Some other alkylated cyclohexanol derivatives are already used as scents and aromas, for example 2-tert-butylcyclohexyl acetate, a commercial scent which has a pine-like, woody fruity fragrance with an additional green note.

2-Isobutylcyclohexyl acetate has a strong fruity note, somewhat reminiscent of raspberries, and a fruity flavor.

4-Tert-butylcyclohexyl acetate is a scent which is sold by various companies and has a sweet, almost creamy woody fragrance with a soft floral note.

Pure cis-4-tert-butylcyclohexyl acetate, which is sold by IFF under the name Vertenex ® HC, has a pure fruity note.

Ortho- and para-tert-butylcyclohexyl caproates have a fruity sweet note with a benzaldehyde-like undertone.

However, the novel compounds of the formula I have substantially different fragrance notes which differ greatly from one another but are extremely interesting.

For example, 2-tert-butyl-4-methylcyclohexyl acetate has a very interesting sensual woody fragrance with a dry tobacco note, the fragrance also being reminiscent of natural musk and civet. 2-tert-butyl-4-methylcyclohexyl propionate has an interesting fruity note reminiscent of apricots and plums.

Hydrogenation of the nucleus of 2-tert-butyl-4-methylphenol or its esters and alkyl ethers is carried out in a conventional manner by catalytic hydrogenation in the presence of a known hydrogenation catalyst, such as Raney nickel or a palladium, rhodium or ruthenium catalyst, preferably a ruthenium catalyst.

Depending on the reaction conditions used, different diastereomer mixtures are obtained, all of which however possess interesting olfactory properties.

If, for example, hydrogenation is carried out under a hydrogen pressure of 50 bar and at 120° C., the isomers shown in the scheme below are obtained in a ratio of A:B:C:D=68:29:2:1. If hydrogenation is carried out under a hydrogen pressure of 50 bar and at 200° C., the ratio A:B:C:D is 52:24:16:8. The isomer ratios were determined in each case by NMR spectroscopy ($^1$H and $^3$C NMR spectra).

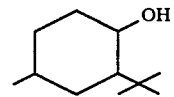
A

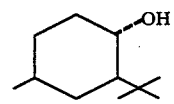
B

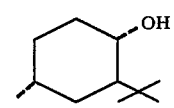
C

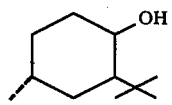

Methylation of the intermediate 2-tert-butyl-4-methylcyclohexanol with an alkyl halide or a dialkyl sulfate gives the corresponding alkyl ethers of the formula I.

These can be obtained in even better yields if 2-tert-butyl-4-methylphenol is first alkylated before being hydrogenated in the nucleus. This 0-alkylation can be carried out by numerous methods described in the literature (cf. Houben-Weyl, Methoden der organischen Chemie, volume VI/3, page 54 et seq [1965]), for example with dialkyl sulfates, alkyl halides, arylsulfonates or salts of alkylsulfuric acids. The substituted phenol ether is then hydrogenated as described above.

2-tert-butyl-4-methylcyclohexyl alkyl ethers have interesting earthy woody vetiver-like notes.

Other scents which are of olfactory interest are obtained by esterifying 2-tert-butyl-4-methylcyclohexanol. This can be done using carboxylic anhydrides, such as acetic anhydride, generally in the presence of catalytic amounts of phosphoric acid or in the presence of another conventional catalyst, such as an alkali metal salt of the corresponding carboxylic acid. The esterification of the cyclohexanols can also be carried out using acyl halides, such as acetyl chloride. This procedure is advantageously carried out in the presence of a tertiary amine, such as pyridine or dimethylaniline, or in the presence of an alkali metal or alkaline earth metal acetate or another organic base.

The resulting esters are advantageously purified by distillation under reduced pressure; they are colorless or pale yellowish liquids and are insoluble in water but soluble in organic solvents, such as alcohols, ethers, ketones, esters and hydrocarbons.

The most interesting member of the novel esters is 2-tert-butyl-4-methylcyclohexyl acetate, which is obtainable, for example, from the 2-tert-butyl-4-methylcyclohexanol diastereomer mixture by acetylation with acetic anhydride and has an interesting sensual woody fragrance with a dry tobacco note and is furthermore reminiscent of natural musk or civet.

The cyclohexanol esters mentioned can also be prepared by acetylation of 2-tert-butyl-4-methylphenol followed by hydrogenation of the nucleus, but the yields in this procedure are substantially poorer.

Because of the fragrance properties described, the novel compounds of the general formula I can advantageously be used as scents or components of scent compositions and perfume oils for cosmetic and industrial applications.

Particularly interesting compounds are:
2-tert-butyl-4-methylcyclohexyl formate,
2-tert-butyl-4-methylcyclohexyl acetate,
2-tert-butyl-4-methylcyclohexyl propionate and
2-tert-butyl-4-methyl-1-methoxycyclohexane.

The Examples which follow illustrate the preparation of some of the novel compounds of the general formula I and include an example of use.

EXAMPLE 1

(a) Preparation of 2-tert-butyl-4-methylcyclohexanol

A mixture of 400 g (2.44 moles) of 2-tert-butyl-4-methylphenol, 400 ml of dioxane and 1 g of ruthenium hydroxide was initially taken in an autoclave and hydrogenated at 120° C. and under a hydrogen pressure of 50 bar until the pressure remained constant (total hydrogenation time about 3 ½ hours). The catalyst was separated off, after which the dioxane was distilled off and the residue was fractionated under 0.01 mbar. After a small initial fraction (15 g with a boiling point up to 60° C./0.01 mbar), 401 g (2.36 moles, corresponding to a yield of 96%) of 2-tert-butyl-4-methylcyclohexanol distilled over at 80°–85° C./0.01 mbar and, after cooling, solidified to a semisolid mass. On the basis of $^{13}C$ NMR spectroscopic data, the product was identified as a diastereomer mixture of the following composition: A:B:C:D = 68:29:2:1

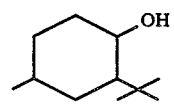

A

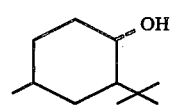

B

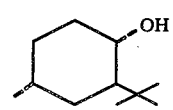

C

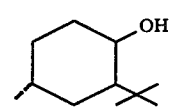

D

Depending on the reaction temperature and hydrogen pressures used, various diastereomer ratios of A, B, C and D were obtained, as shown in the Table below.

TABLE

| Example | Temperature [°C.] | Hydrogen pressure [bar] | Diastereomer ratio A: | B: | C: | D |
|---|---|---|---|---|---|---|
| 1a | 120 | 50 | 68 | 29 | 2 | 1 |
| 1b | 160 | 50 | 61 | 28 | 9 | 2 |
| 1c | 180 | 50 | 58 | 23 | 14 | 5 |
| 1d | 200 | 50 | 53 | 24 | 16 | 7 |

(b) Preparation of 2-tert-butyl-4-methylcylcohexyl formate

A mixture of 920 g (20 moles) of formic acid and 46 g of water was initially taken in a flask, and 170 g (1 mole) of the 2-tert-butyl-4-methylcyclohexanol (diastereomer mixture) obtained as described in 1a) were added dropwise at 25° C. in the course of 30 minutes. The mixture was stirred for 2 days at room temperature, after which the unconverted formic acid was distilled off under reduced pressure (200 mbar) and the residue was fractionated over calcium oxide under 0.03 mbar. 190 g (96% yield) of a diastereomer mixture of three formates were obtained.

The mixture had an interesting woody note.

EXAMPLE 2

2-tert-butyl-4-methylcyclohexyl acetate

A mixture of 680 g (4 moles) of 2-tert-butyl-4-methylcyclohexanol and 612 g (6 moles) of acetic anhydride was heated to 145°–160° C. and the resulting acetic acid was distilled off slowly in the course of 3 hours. When the reaction was complete, the mixture was cooled, the excess acetic anhydride was distilled off under 20 mbar, the residue was cooled and then taken up in 500 ml of diethyl ether, the ether solution was washed acid-free with aqueous sodium bicarbonate solution, the solvent was removed and the residue was then fractionated. After a small initial fraction (13 g of boiling point 30°–45° C./0.005 mbar), 806 g of 2-tert-butyl-4-methylcyclohexyl acetate distilled over at 54°–56° C./0.005 mbar. The refractive index $n_D^{25}$ was 1.4505 and the yield was 95% of theory.

The compound comprised a diastereomer mixture having the same composition as the starting compound and had a very interesting sensual woody fragrance with a dry tobacco note which was also reminiscent of natural musk and civet.

EXAMPLE 3

2-tert-butyl-4-methylcyclohexyl propionate

A mixture of 340 g (2 moles) of 2-tert-butyl-4-methylcyclohexanol and 650 g (5 moles) of propionic anhydride was heated to an internal temperature of 162°–185° C., similarly to Example 2, the resulting propionic acid being distilled off simultaneously in the course of about 3 hours. The mixture was worked up in a similar manner, and the subsequent distillation under reduced pressure gave 411 g (90% yield) of 2-tert-butyl-4-methylcyclohexyl propionate of boiling point 37° C./0.001 mbar and refractive index $n_D^{25}$ 1.4512. The propionate too constituted a diastereomer mixture and had an interesting fruity note reminiscent of apricots and plums.

EXAMPLE 4

(a) 2-tert-butyl-4-methyl-1-phenyl methyl ether 304 g (200 ml, 3.8 moles) of a 50% strength by weight aqueous sodium hydroxide solution were first added dropwise to a solution of 339 g (2.07 moles) of 2-tert-butyl-4-methylphenol in 1 l of toluene, after which 315 g (237 ml, 2.5 moles) of dimethyl sulfate were added dropwise in the course of 1 hour while cooling to 20°–40° C. The reaction mixture was then stirred for a further 12 hours at 25° C., after which it was diluted with 1 l of water and 250 ml of a 20% strength by weight aqueous sodium hydroxide solution and stirred for 1 hour at 25° C., the organic phase was separated off and washed with 100 ml of water, and the toluene was then removed. The residue was subjected to fractional distillation. 300 g of 2-tert-butyl-4-methyl-1-phenyl-methyl ether of boiling point 65° C./2 mbar were obtained.

The compound had an upleasant quinoline note.

(b) 2-tert-butyl-4-methylcyclohexyl methyl ether 300 g of the phenol ether prepared as described in (a) were hydrogenated in the presence of ruthenium hydroxide, as described in Example 1. Removal of the solvent, dioxane, gave a pale yellowish oil which could be fractionated under 0.15 mbar.

The compound had a mild spicy camphoric note.

USE EXAMPLE 1

| Chypre composition | A without I [parts by wt.] | B with I [parts by wt.] |
| --- | --- | --- |
| Cyclododecyl tert-butyl ether (BASF) | 120 | 120 |
| Phenylethyl phenylacetate | 100 | 100 |
| Bergamot oil | 100 | 100 |
| α-ionone | 100 | 100 |
| α-hexylcinnamaldehyde | 100 | 100 |
| Benzyl acetate | 50 | 50 |
| Vetivenyl acetate | 80 | 80 |
| Citronellol | 70 | 70 |
| Linalool | 70 | 70 |
| Cyclopentenyl propionate (BASF) | 50 | 50 |
| Patchouli oil | 30 | 30 |
| Sandalwood oil | 30 | 30 |
| Oakmoss absolute | 30 | 30 |
| Eugenol | 30 | 30 |
| French labdanum oil | 5 | 5 |
| Coriander oil | 5 | 5 |
| Diethyl phthalate | 30 | — |
| 2-tert-butyl-4-methylcyclohexyl acetate | — | 30 |
| | 1,000 | 1,000 |

The addition of 30 parts of 2-tert-butyl-4-methylcyclohexyl acetate (B) instead of diethyl phthalate pleaseantly rounds off the typical chypre composition (A) described above, and the fragrance has more character and body.

USE EXAMPLE 2

| Soap perfume | A without I [parts by wt.] | B with I [parts by wt.] |
| --- | --- | --- |
| Coumarin | 20 | 20 |
| p-tert-butylcyclohexyl acetate | 140 | 140 |
| $C_{11}$ (undecylene) aldehyde, 10% strength in DPG | 30 | 30 |
| Linalool | 100 | 100 |
| Galaxolid ® 50 (JFF) | 50 | 50 |
| Dimethyltetrahydrobenzaldehyde, 10% strength in DPG | 5 | 5 |
| Dihydromyrcenol | 30 | 30 |
| Dimethylheptanol | 15 | 15 |
| Lysmeral* (BASF) | 150 | 150 |
| Isoamyl salicylate | 30 | 30 |
| Cedryl acetate | 70 | 70 |
| Linalyl acetate | 70 | 70 |
| Phenylethyl methyl ether | 20 | 20 |
| Methyl-gamma-ionone | 70 | 70 |
| Phenylethyl alcohol | 70 | 70 |
| Citronellol | 40 | 40 |
| $C_{12}$ aldehyde MNA, 10% strength in DPG | 20 | 20 |
| Vetiveryl acetate | 30 | 30 |
| Anisaldehyde | 10 | 10 |
| 2-tert-butyl-4-methylcyclohexyl acetate | — | 30 |
| Dipropylene glycol (DPG) | 30 | — |

*Trade mark applied for

The addition of as little as 3% by weight of 2-tert-butyl-4-methylcyclohexyl acetate instead of the same amount of dipropylene glycol gives the above soap perfume (A) a substantially fresher note with very much greater radiance.

We claim:

1. A 2-tert-butyl-4-methylcyclohexanol derivative of the formula I

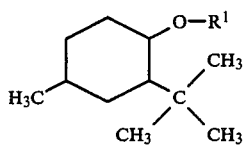 (I)

where $R^1$ is alkyl of 1 to 3 carbon atoms or an acyl group

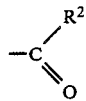

where $R^2$ is alkyl of 1 to 5 carbon atoms.

2. 2-tert-butyl-4-methylcyclohexyl formate.
3. 2-tert-butyl-4-methylcyclohexyl acetate.
4. 2-tert-butyl-4-methylcyclohexyl propionate.
5. 2-tert-butyl-4-methyl-1-methoxycyclohexane.
6. A scent composition which contains a 2-tert-butyl-4-methylcyclohexanol derivative of the formula I as claimed in claim 1.

* * * * *